United States Patent
Mangelsdorf et al.

(10) Patent No.: US 11,318,186 B2
(45) Date of Patent: May 3, 2022

(54) USE OF FGF21 IN METHODS OF INCREASING EXOCRINE PANCREATIC SECRETION

(71) Applicant: Board of Regents, The University of Texas System, Austin, TX (US)

(72) Inventors: David J. Mangelsdorf, Dallas, TX (US); Steven A. Kliewer, Dallas, TX (US); Katie C. Coate, Pelham, AL (US); Genaro Hernandez, Dallas, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 0 days.

(21) Appl. No.: 16/304,080

(22) PCT Filed: May 24, 2017

(86) PCT No.: PCT/US2017/034288
§ 371 (c)(1),
(2) Date: Nov. 21, 2018

(87) PCT Pub. No.: WO2017/205517
PCT Pub. Date: Nov. 30, 2017

(65) Prior Publication Data
US 2019/0201490 A1 Jul. 4, 2019

Related U.S. Application Data

(60) Provisional application No. 62/341,591, filed on May 25, 2016.

(51) Int. Cl.
*A61K 38/18* (2006.01)
*C07K 14/50* (2006.01)
*A61P 1/18* (2006.01)
*A61K 9/00* (2006.01)

(52) U.S. Cl.
CPC ........ *A61K 38/1825* (2013.01); *A61K 9/0019* (2013.01); *A61K 9/0053* (2013.01); *A61P 1/18* (2018.01); *C07K 14/50* (2013.01)

(58) Field of Classification Search
None
See application file for complete search history.

(56) References Cited

U.S. PATENT DOCUMENTS

| | | |
|---|---|---|
| 2002/0164713 A1 | 11/2002 | Itoh et al. |
| 2012/0172298 A1 | 7/2012 | Andersen et al. |
| 2013/0035373 A1 | 2/2013 | Collard et al. |
| 2013/0079500 A1 | 3/2013 | Boettcher et al. |
| 2013/0129724 A1 | 5/2013 | Boettcher et al. |
| 2015/0166622 A1 | 6/2015 | Boettcher et al. |
| 2015/0284442 A1 | 10/2015 | Ling et al. |

FOREIGN PATENT DOCUMENTS

| | | |
|---|---|---|
| WO | 03/011213 A2 | 2/2003 |
| WO | 2011/154439 A2 | 12/2011 |
| WO | WO 2012/066075 | 5/2012 |
| WO | WO 2015/195509 A2 | 12/2015 |
| WO | WO 2016/065106 A1 | 4/2016 |
| WO | WO 2016/065326 A1 | 4/2016 |

OTHER PUBLICATIONS

Nieto et al. Gastroenterol. Hepatol. 4(2): 1-7, 2016.*
Struyvenberg et al. BMC Medicine 15:29, 2017 (8 pages).*
Extended European Search Report regarding Europe Application No. 17803516 dated Feb. 11, 2020.
Coate et al., "FGF21 is an Exocrine Pancreas Secretagogue", Cell Metabolism, Cell Press, 25(2):472-480, 2017.
Johnson et al., "Fibroblast Growth Factor 21 Reduces the Severity of Cerulein-Induced Pancreatitis in Mice", Gastroenterology:Official Publication of the American Gastroenterological Association, Wilkins & Wilkins, 137(5):1795-1804, 2009.
Woo et al., "Fibroblast Growth Factor 21 as an emerging metabolic regulator:clinical perspectives", Clinical Endocrinology 78(4):489-496, 2013.
Adams, et al., "LY2405319, an Engineered FGF21 Variant, improves the Metabolic Status of Diabetic Monkeys," PLoS ONE 8(6):e65763 (2013).
International Preliminary Report on Patentability for International Application No. PCT/US2017/034288 dated Aug. 16, 2017.
International Search Report and Wiilien Opinion for International Application No. PCT/US2017/034288 dated Aug. 16, 2017.
Fisher and Maratos-Flier, "Understanding the Physiology of FGF21," Annual Review of Physiology 78:223-241 (2016).
Johnson, et al., "Fibroblast Growth Factor 21 Reduces the Severity of Cerulein-Induced Pancreatitis in Mice," Gastroenterology 137(5):1795-804 (2009).
Johnson, et al., "Silencing the Fibroblast Growth Factor 21 Gene is an Underlying Cause of Acinar Cell Injury in Mice Lacking MIST1," Am J Physiol Endocrinol Metab 306(8):E916-928 (2014).
Kim and Lee, "FGF21 as a Mediator of Adaptive Responses to Stress and Metabolic Benefits of Anti-Diabetic Drugs," Journal of Endocrinology 226(1):R1-16 (2015).

(Continued)

*Primary Examiner* — Christine J Saoud
(74) *Attorney, Agent, or Firm* — Dentons US LLP (57) ABSTRACT

The present invention relates to the treatment of secretory disorders, and provides novel methods of treatment of these disorders comprising the administration of fibroblast growth factor 21 (FGF21) or derivatives thereof. The methods of the invention are useful in conditions including exocrine pancreatic insufficiency (EPI), for example EPI resulting from cystic fibrosis, alcoholism, pancreatitis, pancreatic cancer, gallstones, celiac disease, high triglycerides, or lupus. The methods of the present invention find further utility in the treatment of salivary flow disorders, for example Sjorgen's syndrome, and the treatment of EPI or pancreatitis resulting from surgical procedures.

15 Claims, 6 Drawing Sheets
Specification includes a Sequence Listing.

(56) References Cited

OTHER PUBLICATIONS

Sun, et al., "Autofluorescence Imaging of Live Pancreatic Islets Reveals Fibroblast Growth Factor-231 (FGF21)-Induced Metabolism," Biophys J 103(11):2379-88 (2012).

Waldron et al., "Endoplasmic Reticulum Stress and the Unfolded Protein Response in Exocrine Pancreas Physiology and Pancreatitis," Pancreapedia: Exocrine Pancreas Knowledge Base, DOI: 10.3998/panc.2015.41 (2015).

Kharitonenkov et al., "FGF-21 as a Novel Metabolic Regulator," The Journal of Clinical Investigation, 115(6):1627-2635 (2005).

Coskun et al., "Fibroblast Growth Factor 21 Corrects Obesity in Mice," Endocrinology, 149(12): 6018-6027 (2008).

Hyun and Lee, "Experimental Models of Pancreatitis," Clin Endosc, 47: 212-216 (2014).

Jin et al., "Exposure to Radiocontrast Agents Induces Pancreatic Inflammation by Activation of Nuclear Factor-kB, Calcium Signaling, and Calcineurin," Gastroenterology, 49(3): 753-764 (2015).

* cited by examiner

SEQUENCE LISTING

<160> NUMBER OF SEQ ID NOS: 1

<210> SEQ ID NO 1
<211> LENGTH: 20
<212> TYPE: DNA
<213> ORGANISM: Artificial sequence
<220> FEATURE:
<223> OTHER INFORMATION: Guide RNA sequence

<400> SEQUENCE: 1
agtttcaaga ttcactccgg                                               20

USE OF FGF21 IN METHODS OF INCREASING EXOCRINE PANCREATIC SECRETION

REFERENCE TO RELATED APPLICATION

This application is a 371 National Stage application of International Application No. PCT/US2017/034288, filed May 24, 2017, which application claims benefit of U.S. Provisional Application No. 62/341,591, filed May 25, 2016, each of which is herein incorporated by reference in its entirety.

STATEMENT OF GOVERNMENT RIGHTS

This invention was made with Government support under Grant No. R01DK067158 awarded by the National Institutes of Health. The Government has certain rights in the invention.

INCORPORATION OF SEQUENCE LISTING

A sequence listing containing the file named "UTSW013WO_ST25.txt" which is 482 bytes (measured in MS-Windows®) and created on May 24, 2017, and comprises one sequence, and is incorporated herein by reference in its entirety.

FIELD OF THE INVENTION

The present invention relates generally to therapeutic agents for the treatment of secretory disorders. More particularly, the invention relates to the provision of secretagogues which do not detrimentally induce protein synthesis, and methods of treatment employing these compounds.

BACKGROUND

Existing therapies for the treatment of secretory disorders, including exocrine pancreatic insufficiency (EPI) and salivary flow disorders, do not prevent or reverse the progression of these diseases. Secretory disorders often result from, or are comorbid with, other disease states including cystic fibrosis, alcoholism, pancreatitis, pancreatic cancer, gallstones, celiac disease, high triglycerides, lupus, or are associated with a surgical procedure. In some cases, secretory disorders, for example pancreatitis resulting from cystic fibrosis, may be fatal. In others, such as EPI resulting from alcoholism, patients are subject to standard hospitalization, sometimes in intensive care units, until their pain and blood profiles normalize.

While secretagogues such as cholecystokinin (CCK) are known, these compounds increase protein synthesis and lead to proteotoxicity which exacerbates the symptoms of secretory disorders. A need therefore exists for secretagogues which do not lead to proteotoxicity or an increase in endoplasmic reticulum (ER) stress.

SUMMARY OF THE INVENTION

In one aspect, the present invention provides a method of treating a secretory disorder in a subject, comprising administering to said subject a therapeutically sufficient amount of fibroblast growth factor 21 (FGF21) or a derivative of FGF21. In certain embodiments, the secretory disorder is exocrine pancreatic insufficiency (EPI), for example EPI comorbid with a disorder selected from the group consisting of: cystic fibrosis, alcoholism, pancreatitis, pancreatic cancer, gallstones, celiac disease, high triglycerides, and lupus. In other embodiments the EPI results from a surgical procedure, for example endoscopic retrograde cholangiopancreatography (ERCP). In further embodiments, the secretory disorder is a salivary flow disorder, for example a salivary flow disorder comorbid with a disorder selected from the group consisting of: rheumatoid arthritis, lupus, and cancer, such as Sjorgen's syndrome.

In certain embodiments, administering a therapeutically sufficient amount of FGF21 comprises local, regional, systemic, or continual administration. In some embodiments, administering comprises providing a single dose. Administering according to the methods provided further comprises oral, intravenous or intramuscular administration. In some embodiments, the FGF21 or FGF21 derivative is administered at a dosage of between 0.1 mg and 300 mg, for example at a dosage of between 1 mg and 200 mg. In further embodiments, the derivative of FGF21 is a long-acting derivative of FGF21. Administering according to embodiments of the present invention comprises providing a pharmaceutical composition comprising FGF21 or a derivative of FGF21, dispersed in a pharmaceutically acceptable carrier, buffer or diluent.

In yet further embodiments, the methods provided by the invention comprise providing FGF21 together with a second therapy, for example wherein the second therapy is provided prior to administering the FGF21 or derivative of FGF21, or wherein the second therapy is provided after administering the FGF21 or a derivative of FGF21, or wherein the second therapy is provided at the same time as the FGF21 or a derivative of FGF21.

In certain embodiments, the invention provides methods of treating a secretory disorder in a subject, wherein said subject is a human.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 1 shows a CRISPR/Cas9-mediated knock-in strategy for the generation of KLB-T mice. The single guide RNA (SEQ ID NO: 1) with a sequence targeted to the 3' UTR of Klb exon 5, which contained a protospacer adjacent motif (PAM), was used to induce recombination of the HDR template (Donor DNA) containing Tdtomato. The HDR had a 2 Kb left arm (HA-L) and 3 Kb right arm of homology (HA-R).

FIG. 2 demonstrates that FGF21 regulates digestive enzyme levels. (A, B) H&E staining of pancreas imaged at 20× magnification with quantification of eosinophilic area fraction (A) and western blot quantification of amylase and lipase levels (B) in wild type (WT) and Fgf21-knockout (KO) mice after an overnight fast and 2 hour refeeding period. (C, D) H&E staining of pancreas imaged at 20× magnification with quantification of eosinophilic area fraction (C) and western blot quantification of amylase and lipase levels (D) in WT and Fgf21-KO mice treated with vehicle or 1 mg/kg recombinant FGF21 twice per day for two consecutive days. (E-G) pancreatic FGF21 mRNA (E), pancreatic FGF21 protein (F) and plasma FGF21 (G) levels in WT mice after an overnight fast and 2 hour refeeding period. (H) FGF21 protein levels in pancreatic juice and plasma before (Basal) or after 15 min CCK treatment of ad-lib fed WT mice. Results are expressed as means±S.E.M. n=3-6 mice/group for all experiments. *, p<0.05; , p<0.01; *, p<0.001; ****, p<0.0001.

FIG. 4 demonstrates that FGF21 triggers intracellular calcium release via an FGFR-PLC-IP$_3$R pathway. (A-E) Calcium release in AR42J cells was measured by the calcium indicator Fluo4-AM signal minus background fluorescence normalized to baseline fluorescence (ΔF/F0) for 2 minutes at 10× magnification. Cells were imaged for 10 seconds and then treated with either 1 µg/ml FGF21 (left panels) or 100 pM CCK (right panels). Black arrows indicate the start of treatment. In (B-E), cells were treated 30 minutes prior and during imaging with 1 µM PD173074 (B), 10 µM L-364,718 (C), 10 µM U73122 (D) or 100 µM 2-APB (E). Calcium transients are expressed as the mean calcium release of 50-200 cell clusters/group with each cluster containing 5-20 cells. Similar results were obtained in 2 independent experiments. (F) Western blot images and quantification of pancreatic total (T) and phospho (p) PLCγ$_1$ and PLCβ$_3$ and p-ERK1/2 from WT mice treated with 1 mg/kg FGF21 or 5 µg/kg CCK (i.p.) for 15 min. Hsp90 is the loading control. Results are expressed as means±SEM n=4 mice/group. *p<0.05; p<0.01; *p<0.001. (G) Model for the action of FGF21 on the acinar cell to stimulate digestive enzyme secretion.

FIG. 5 demonstrates stimulation of calcium release from AR42J cells. Calcium was measured by subtracting the background fluorescence from the Fluo4-AM signal normalized to baseline fluorescence (ΔF/F0) for 2 minutes at 10× magnification. Cells were treated 30 minutes prior to imaging with 1 µM PD173074, 10 µM L-364,718, 10 µM U73122 or 100 µM 2-APB followed by treatment with vehicle (black arrow). Calcium transients are expressed as the mean calcium release of 50-200 cell clusters/group with each cluster containing 5-20 cells. Similar results were obtained in 2 independent experiments.

DETAILED DESCRIPTION

Exocrine pancreatic insufficiency (EPI) is the inability of the exocrine pancreas to secrete and deliver digestive enzymes to the small intestine where they break down nutrients during digestion for their absorption. Several different disorders, including alcoholism and cystic fibrosis, can give rise to EPI, and patients with this condition fall into a state of malnutrition if not treated.

Existing therapies for the treatment of EPI do not prevent or reverse progression of the disorder. This is in part because known treatments directed to increasing exocrine pancreatic secretion also function to increase protein synthesis, resulting in proteotoxicity. As a result, EPI that develops in cases of cystic fibrosis is typically fatal, while patients suffering from other causes of acute or chronic EPI are subject to hospitalization, sometimes in intensive care units. The fact that EPI cannot be treated directly can lead to pancreatic cancer, and existing therapies are not able to prevent this progression.

The present inventors have surprisingly discovered that fibroblast growth factor 21 (FGF21) is capable of increasing exocrine pancreatic secretion without detrimentally increasing protein synthesis. FGF21 is therefore uniquely able to induce secretion and pancreatic juice flow without causing proteotoxicity. While FGF21 was previously believed to function via an anti-inflammatory mechanism (Fisher, et al., *Annu Rev Physiol* 78: 223-241, 2016; Johnson et al., *Gastroenterology* 137(5): 1795-1804, 2009), the instant disclosure shows for the first time that FGF21 functions via a secretory mechanism. Surprisingly, and different from classical post-prandial secretagogues including cholecystokinin (CCK), FGF21 acts to reduce pancreatic endoplasmic reticulum (ER) stress (proteotoxicity) by inducing secretion without protein synthesis, which relieves the excessive protein load common to EPI. The invention further provides novel methods of treating secretory disorders such as EPI using FGF21.

Thus, the present invention has shown for the first time that FGF21 therapy has the potential to prevent the progression of chronic pancreatitis to pancreatic cancer. FGF21 is further shown to be useful for other secretory disorders or diseases, such as dry mouth disease (Sjorgen's syndrome), where the salivary glands fail to produce saliva. Methods of treating exocrine pancreatic insufficiency comorbid with cystic fibrosis, alcoholism, pancreatitis, pancreatic cancer, gallstones, celiac disease, high triglycerides, or lupus; or resulting from a surgical procedure are further provided.

I. Fibroblast Growth Factor 21 (FGF21)

Fibroblast growth factor 21 (FGF21) is a hormone whose synthesis and secretion are triggered by diverse metabolic and cellular stresses, ranging from starvation to mitochondrial and ER stress. FGF21 acts through a cell surface receptor composed of a conventional FGF receptor (FGFR) with tyrosine kinase activity in complex with β-Klotho, a single-pass transmembrane protein. FGF21, β-Klotho and FGFRs are co-expressed in the exocrine pancreas, suggesting that pancreatic acinar cells are a site of FGF21 action in vivo. Accordingly, FGF21 mRNA levels are induced in whole pancreas during the transition from the fasted to the fed state and in isolated acinar cells after thapsigargin treatment, which induces ER stress. While pharmacologic administration of FGF21 attenuates acinar cell injury in genetic and pharmacologic-induced mouse models, the biological function of FGF21 in exocrine pancreas is not known.

The present inventors have discovered that FGF21 functions as a secretagogue in the exocrine pancreas to induce secretion and pancreatic juice flow. It is further shown in the instant disclosure that FGF21 targets a receptor that is different from other secretagogues, and therefore does not increase protein synthesis, resulting in an ability to relieve proteotoxic stress. Life-threatening conditions of pancreatitis in which this secretory process is compromised include cystic fibrosis and alcoholism, and the ability of FGF21 to promote pancreatic secretion and juice flow will relieve these conditions. FGF21 is further useful in other tissues with secretory capabilities, where the FGF21 receptor complex FGFR1/β-Klotho is expressed, including the salivary glands. Thus, FGF21 is shown for the first time in the instant disclosure to be an effective therapy for patients with secretory and flow disorders.

II. Therapeutic Use of FGF21

Secretory and flow disorders which are shown in the instant disclosure to be amendable to treatment with FGF21 therapy include exocrine pancreatic insufficiency, for example resulting from or comorbid with cystic fibrosis, alcoholism, pancreatitis, pancreatic cancer, gallstones, celiac disease, high triglycerides, or lupus. Other secretory disorders amenable to FGF21 treatment include salivary flow disorders, including Sjorgen's syndrome, and secretory disorders resulting from surgical procedures, including EPI resulting from endoscopic retrograde cholangiopancreatography (ERCP). Subjects suffering from these disorders may be treated with FGF21, or a derivative of FGF21, according to the methods provided herein to alleviate symptoms of the disorder.

Based on the FGF21 bioactivities provided in the instant disclosure in vitro and in vivo, FGF21 formulations of the present invention may be used alone or in combination with other therapeutic agents in the treatment of the following conditions:

Exocrine Pancreatic Insufficiency (EPI)

The FGF21 formulations described herein are further useful in the treatment of EPI, for example resulting from or comorbid with cystic fibrosis, alcoholism, pancreatitis, pancreatic cancer, gallstones, celiac disease, high triglycerides, or lupus. EPI is the inability of the exocrine pancreas to secrete and deliver digestive enzymes to the small intestine where they facilitate the digestion and absorption of nutrients. Thus, a patient with EPI will experience malnutrition. EPI can arise from other pancreatic conditions such as pancreatitis and cystic fibrosis. Existing therapies for these conditions are limited to ameliorating symptoms, and there are no known treatments which address the disorder directly or prevent progression of EPI. The FGF21 compositions and derivatives provided herein stimulate digestive enzyme secretion and pancreatic juice flow, and can be used therapeutically to reestablish digestive enzyme secretion and flow in patients with EPI. The FGF21 formulations and therapies of the present invention may be used alone or in combination with other agents to treat or prevent EPI.

Salivary Flow Disorders

As described herein, FGF21 or derivatives thereof act as a secretagogue to increase secretion without increasing proteotoxicity. FGF21 and derivatives thereof are therefore useful in the treatment of salivary flow disorders including Sjorgen's disease (dry mouth disease). The FGF21 formulations and therapies of the present invention may be used alone or in combination with other agents to treat or prevent salivary flow diseases.

Endoscopic Retrograde Cholangiopancreatography

Endoscopic retrograde cholangiopancreatography (ERCP) is a technique used in the clinic to study bile ducts, pancreatic ducts and gallbladder. The technique consists of introducing an endoscope through a patient's mouth, passing through the esophagus and stomach in order to access the duodenum where the ducts drain. The endoscope is used to deliver a radio-contrast agent that will facilitate the visualization of the ducts. One of the common complications following this procedure is pancreatitis in about 10% of patients that undergo this procedure.

The instant disclosure demonstrates that treatment with FGF21 or derivatives thereof reduces pancreatitis. FGF21 has been approved for other clinical indications and tested for safety and efficacy in human subjects. Thus, treatment with the FGF21 formulations provided herein can be used to prevent or reduce the pancreatitis elicited by ERCP. In certain embodiments the FGF21 treatment may be preventative, and may consist of administering FGF21 or a derivative thereof prior to a surgical procedure which may elicit pancreatitis.

Acute or Chronic Pancreatitis

There has been a significant increase in the incidence of both acute and chronic pancreatitis in the United States where about 50 out of every 100,000 individuals will experience pancreatitis. The current standard of care for both chronic and acute pancreatitis is limited to hospitalizations whenever a patient experiences some of the several complications from this disease such as abdominal pain, vomiting and nausea. The FGF21 formulations and derivatives provided herein are useful in the preventing and treatment of acute and chronic pancreatitis. FGF21 and derivatives thereof are shown herein be effective in lowering both inflammation and damage to the pancreas in rodent models of pancreatitis.

As described herein, FGF21 or derivatives thereof act as a secretagogue to increase secretion without increasing proteotoxicity. FGF21 and derivatives thereof are therefore useful in the treatment of acute or chronic pancreatitis, for example resulting from or comorbid with cystic fibrosis, alcoholism, pancreatitis, pancreatic cancer, gallstones, celiac disease, high triglycerides, or lupus. The FGF21 formulations and therapies of the present invention may be used alone or in combination with other agents to treat or prevent acute or chronic pancreatitis.

Cancer

The FGF21 formulations described herein are further useful in the treatment of cancer or pre-cancerous disorders, for example pancreatic cancer resulting from progression of EPI. Existing therapies for are directed to symptoms, and do not treat the underlying causes of the EPI or prevent progression to pancreatic cancer. The FGF21 formulations and therapies of the present invention may be used alone or in combination with other agents to treat or prevent cancer or pre-cancerous disorders.

III. Exocrine Pancreatic Insufficiency and Proteotoxicity

EPI is the inability of the exocrine pancreas to secrete and deliver digestive enzymes to the small intestine where they break down nutrients during digestion for their absorption. As a result, patients suffering from EPI fall into a state of malnutrition if not treated. Several different diseases such as alcoholism and cystic fibrosis can give rise to EPI. The FGF21 or FGF21 derivative formulations provided herein act to prevent or treat EPI by inducing pancreatic secretion and flow. FGF21 acts via distinct receptor from classical pre-prandial secretagogues such a CCK, and this receptor is unaffected during chronic pancreatitis or cystic fibrosis. This allows for the reestablishment of normal pancreatic secretion.

In the case of EPI, the only treatment available is pancreatic enzyme replacement therapy (PERT). PERT only ameliorates the state of malnutrition in patients with EPI but does not address pancreatic malfunction. The fact that pancreatitis cannot be treated directly with existing therapies can lead to pancreatic cancer.

Pancreatic acinar cells synthesize and secrete more protein than any other adult cell type, meaning that it is essential that they have mechanisms to minimize protein misfolding and associated endoplasmic reticulum (ER) stress. Moreover, classical pancreatic secretagogues used as therapies for secretory disorders induce protein synthesis, leading to proteotoxicity. The present inventors have shown for the first time in the instant disclosure that FGF21 or derivatives thereof can be used to induce secretion in the exocrine pancreas, without detrimental proteotoxicity.

IV. Pharmaceutical Compositions

The FGF21 or FGF21 derivatives of the present invention can be administered to treat secretory disorders including EPI, salivary flow disorders, or EPI resulting from surgical procedures as described herein. They can be administered by any conventional methods available for use in conjunction with pharmaceuticals, either as individual therapeutically active ingredients or in a combination of therapeutically active ingredients. They can be administered alone but are generally administered with a pharmaceutically acceptable carrier selected on the basis of the selected route of administration and standard pharmaceutical practice.

Aqueous compositions of the present invention will have an effective amount of FGF21 or an FGF21 derivative to function as a secretagogue without inducing proteotoxicity. Such compositions will generally be dissolved or dispersed in a pharmaceutically acceptable carrier or aqueous medium.

The phrases "pharmaceutically acceptable" or "pharmacologically acceptable" refer to molecular entities and compositions that do not produce an adverse, allergic or other undesirable reaction when administered to an animal, or human, as appropriate. As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredients, its use in the therapeutic compositions is contemplated. Supplementary active ingredients, such as other anti-hypertensive, anti-inflammatory, or anti-growth agents, can also be incorporated into the compositions.

In addition to the compounds formulated for parenteral administration, such as intravenous or intramuscular injection, other pharmaceutically acceptable forms include, e.g., tablets or other solids for oral administration; time release capsules; and any other form currently used, including creams, lotions, mouthwashes, inhalants, lipid carriers, liposomes and the like.

Oral Administration

In certain embodiments, active compounds of the present invention may be administered orally. This is contemplated for agents which are generally resistant, or have been rendered resistant, to proteolysis by digestive enzymes. Such compounds are contemplated to include all those compounds, or drugs, that are available in tablet form from the manufacturer and derivatives and analogues thereof.

For oral administration, the active compounds of the present invention may be administered, for example, with an inert diluent or with an assimilable edible carrier, or they may be enclosed in hard or soft shell gelatin capsule, or compressed into tablets, or incorporated directly with the food of the diet. For oral therapeutic administration, the active compounds may be incorporated with excipients and used in the form of ingestible tablets, buccal tables, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of the unit. The amount of active compounds in such therapeutically useful compositions is such that a suitable dosage will be obtained.

Tablets, troches, pills, capsules and the like may also contain the following: a binder, as gum tragacanth, acacia, cornstarch, or gelatin; excipients, such as dicalcium phosphate; a disintegrating agent, such as corn starch, potato starch, alginic acid and the like; a lubricant, such as magnesium stearate; and a sweetening agent, such as sucrose, lactose or saccharin may be added or a flavoring agent, such as peppermint, oil of wintergreen, or cherry flavoring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup of elixir may contain the active compounds sucrose as a sweetening agent methyl and propylparabens as preservatives, a dye and flavoring, such as cherry or orange flavor. Of course, any material used in preparing any dosage unit form should be pharmaceutically pure and substantially non-toxic in the amounts employed. In addition, the active compounds may be incorporated into sustained-release preparation and formulations.

Upon formulation, the FGF21 or FGF21 derivative of the present invention will be administered in a manner compatible with the dosage formulation and in such amount as is therapeutically effective. The formulations are easily administered in a variety of dosage forms, such as those described below in specific examples.

Parenteral Administration

The active compounds of the present invention may also be formulated for parenteral administration, e.g., formulated for injection via the intravenous, intramuscular, subcutaneous, or even intraperitoneal routes. The preparation of an aqueous composition that contains FGF21 or an FGF21 derivative of the present invention as an active ingredient will be known to those of skill in the art in light of the present disclosure. Typically, such compositions can be prepared as injectables, either as liquid solutions or suspensions; solid forms suitable for using to prepare solutions or suspensions upon the addition of a liquid prior to injection can also be prepared; and the preparations can also be emulsified.

Solutions of the active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

In some forms, it will be desirable to formulate the compounds of the present invention in salt form, generally to improve the solubility and bioavailability and to provide an active drug form more readily assimilated. As used herein, the term "pharmaceutically acceptable salt" refers to compounds which are formed from acidifying FGF21 or a derivative thereof in a solution with suitable physiologically tolerated acids. Suitable physiologically tolerated acids are organic and inorganic acids, such as hydrochloric acid, sulfuric acid, phosphoric acid, acetic acid, citric acid, oxalic acid, malonic acid, salicylic acid, maleic acid, methane sulfonic acid, isothionic acid, lactic acid, gluconic acid, glucuronic acid, amidosulfuric acid, benzoic acid, tartaric acid and pamoaic acid. Typically, such salt forms of the active compound will be provided or mixed prior to use.

The pharmaceutical forms suitable for injectable use include sterile aqueous solutions or dispersions; formulations including sesame oil, peanut oil, or aqueous propylene glycol; and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms, such as bacteria and fungi.

The active compounds may be formulated into a composition in a neutral or salt form. Pharmaceutically acceptable salts, include the acid addition salts and which are formed with inorganic acids such as, for example, hydrochloric or phosphoric acids, or such organic acids as acetic, oxalic, tartaric, mandelic, and the like.

The compounds of the present invention may also be formulated into a composition comprising liposomes or any other lipid carrier. Liposomes include: multivesicular liposomes, multilamellar liposomes, and unilamellar liposomes.

The carrier can also be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial ad antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

Upon formulation, solutions will be administered in a manner compatible with the dosage formulation and in such amount as is therapeutically effective. The formulations are easily administered in a variety of dosage forms, such as the type of injectable solutions described above, with even drug release capsules and the like being employable.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this regard, sterile aqueous media which can be employed will be known to those of skill in the art in light of the present disclosure. For example, one dosage could be dissolved in 1 mL of isotonic NaCl solution and either added to 1000 mL of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the individual subject.

V. Therapies

One way of achieving this is by combining new drugs with the traditional therapies. In the context of the present invention, it is contemplated that FGF21 or derivatives thereof provided by the invention could be used in combination with new or existing pharmaceutical agents, surgery, chemotherapy, radiotherapy, and/or gene therapy.

An "effective amount" or a "therapeutically sufficient amount" are those amounts of a compound sufficient to produce a therapeutic benefit (e.g., effective to function as anti-hypertensive and/or anti-inflammatory and/or anti-growth agent). An effective amount, in the context of treating a subject, is sufficient to produce a therapeutic benefit. The term "therapeutic benefit" as used herein refers to anything that promotes or enhances the well-being of the subject with respect to the medical treatment of the subject's disease. A nonexhaustive list of examples of therapeutic benefits includes extension of the patients life by any period of time; decrease or delay in development of disease; decrease in hypertension; decrease in inflammation; decrease in cell growth or proliferation; and/or a decrease in pain to the subject that can be attributed to the patient's condition.

The term "about" is used to indicate that a value includes the standard deviation of error for the device or method being employed to determine the value. The use of the term "or" in the claims is used to mean "and/or" unless explicitly indicated to refer to alternatives only or the alternatives are mutually exclusive, although the disclosure supports a definition that refers to only alternatives and to "and/or." When used in conjunction with the word "comprising" or other open language in the claims, the words "a" and "an" denote "one or more," unless specifically noted. The terms "comprise," "have" and "include" are open-ended linking verbs. Any forms or tenses of one or more of these verbs, such as "comprises," "comprising," "has," "having," "includes" and "including," are also open-ended. For example, any method that "comprises," "has" or "includes" one or more steps is not limited to possessing only those one or more steps and also covers other unlisted steps. Similarly, any plant that "comprises," "has" or "includes" one or more traits is not limited to possessing only those one or more traits and covers other unlisted traits.

The terms "inhibiting," "reducing," or "prevention," or any variation of these terms, when used in the claims and/or the specification includes any measurable decrease or complete inhibition to achieve a desired result.

The term "effective," as that term is used in the specification and/or claims, means adequate to accomplish a desired, expected, or intended result.

Other objects, features and advantages of the present invention will become apparent from this detailed description and examples provided below. It should be understood, however, that the detailed description and any specific examples provided, while indicating specific embodiments of the invention, are given by way of illustration only, since various changes and modifications within the spirit and scope of the invention will become apparent to those skilled in the art from this detailed description.

EXAMPLES

Example 1. Fgf21-Knockout and Fgf21-Transgenic Mice

Mouse Studies

Fgf21-knockout (KO) mice (Potthoff, et al., *Proc Natl Acad Sci USA* 106, 10853-10858, 2009), Fgf21-transgenic (Tg) mice (Inagaki, et al., *Cell Metab* 5, 415-425, 2007), KLB-T and WT littermates were maintained on a C57B1/6J background. β-Klotho-KO and heterozygous littermates were kept on a mixed C57BL/6J;129/Sv background (Ding, et al., *Cell Metab* 16, 387-393, 2012). All mice were housed in a pathogen-free facility and fed a standard chow diet (Harlan Teklad 2916). For fasting refeeding experiments, mice were fasted overnight and then refed for 2 hours with standard chow diet. Acute pancreatitis was induced by administration of seven hourly intraperitoneal injections of 50 µg/kg cerulein (Sigma), whereas mice in the control group were injected with saline. FGF21 in plasma was measured using a mouse FGF21 ELISA kit (Biovendor). Male mice were used for all experiments.

Figure 1:
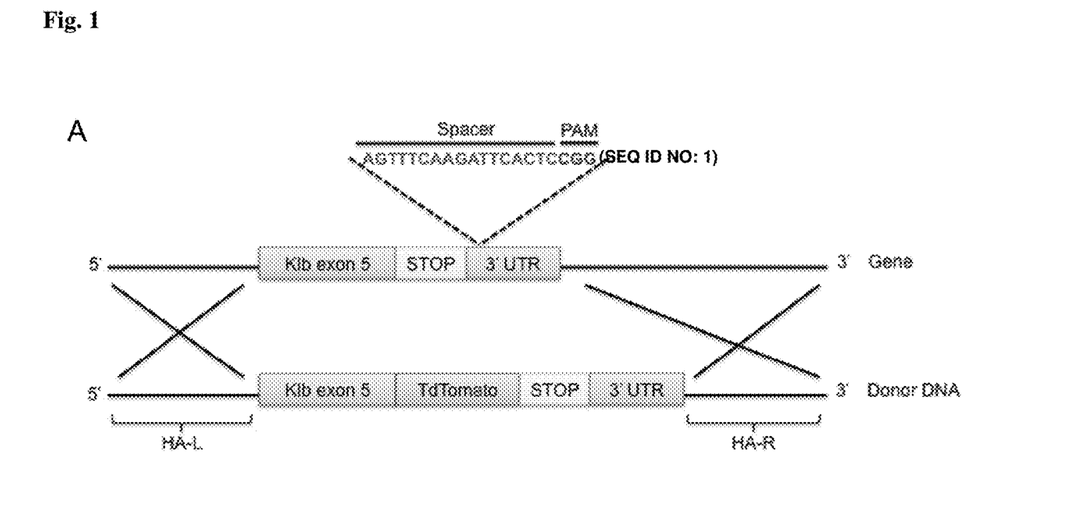

Beta-Klotho-Tdtomato (KLB-T) reporter mice were generated using the CRISPR/Cas9 knock-in method as described (Yang, et al., *Cell* 154, 1370-1379, 2013). The coding region of the Tdtomato gene was fused in-frame to the 3' end of the last coding exon (exon 5) of the Klb gene. A single guide RNA, having the sequence of SEQ ID NO: 1, targeting the 3' UTR of Klb exon 5 was microinjected in C57B1/6J zygotes in conjunction with Cas9 mRNA (Trilink Bio) and a circular homology-directed repair (HDR) template containing Klb exon 5 fused to Tdtomato bounded by left (2 kb) and right (3 kb) arms of homologous sequence (FIG. 1). The injected zygotes were implanted into pseudo-pregnant female C57B1/6J mice. Mice born from these microinjections were screened by PCR from tail DNA to verify HDR template insertion and germline transmission was confirmed in the second generation of breeding with WT C57B1/6J mice to eliminate any potential mosaicism. For this study, male homozygous KLB-T and their WT littermates were used.

Pancreatic Juice Collection

Mice were injected with vehicle (10 mM $Na_2HPO_4$, 2% [w/v] glycerol, pH 7.6) or 1 mg/kg human recombinant FGF21 (Novo Nordisk) subcutaneously twice per day for two consecutive days. Mice were fasted for 6 hours, and pancreatic juice was collected for 15 minutes. The final injection of vehicle or FGF21 was given 1 hour prior to pancreatic juice collection.

Measurement of Pancreatic Protein Synthesis

Pancreatic protein synthesis was measured by the flooding dose method using $^3$H-phenylalanine (Sans, et al., *American journal of physiology* 287, G667-675, 2004).

Real-Time Quantitative PCR

RNA from pancreas was extracted using RNA-Stat 60 (IsoTex Diagnostics). cDNA was generated from RNA (2 µg) using the High-Capacity cDNA Reverse Transcription Kit (Life Technologies). qPCR was performed by the SYBR green method as described (Bookout, et al. *Current protocols in molecular biology*/ed. Ausubel, Chapter 15, Unit 15-18, 2006).

Histology

Mouse pancreas was fixed in 10% neutral buffered formalin overnight and then paraffin embedded, sectioned and hematoxylin and eosin stained. For fresh frozen histology, the pancreas was quickly dissected, snap frozen in cooled isopentane and sectioned at 14-16 µm. The sections were then fixed in 10% neutral buffered formalin for 15 min at 4° C., washed 3 times in 1× PBS and mounted with Vectashield mounting medium with DAPI (Vector Laboratories). Images were acquired with a Zeiss Axioscan Z1 slide scanner at a 20× magnification. Quantification of the eosinophilic area was performed using Image J.

Immunoblotting

Pancreas was homogenized using Fastprep-24 lysing matrix bead tubes (MP Biomedicals) in 1× RIPA buffer (Cell Signaling Technology) supplemented with a cocktail of protease and phosphatase inhibitors (Roche). Protein lysate concentrations were measured using the DC Protein Assay (Biorad). Equal protein amounts were loaded and electrophoresed in a 420% SDS-polyacrylamide gel (Biorad) and transferred to nitrocellulose membranes (Biorad). Membranes were blocked with 5% BSA in TBST for 1 hour. Probing of membranes with antibodies against FGF21, amylase and lipase (Santa Cruz); β-actin (Abcam); p-EIF2α, p-ERK1/2, and p-eIF4E-BP1 (Cell Signaling Technology) was performed overnight at 4° C. Membranes were then incubated with HRP-conjugated secondary antibodies (Cell Signaling Technology) against the primary antibody's host species for 1 hour. Membranes were developed using the Super Signal West Chemiluminescence Kit (Thermo) and signal was detected with an ImageQuant LAS4000 luminescent imager (General Electric). Quantification was done using Image J.

Statistical Analyses

Student's T-Test was used for two-group analyses. One-way and two-way ANOVA with Newman-Keuls post-hoc correction (Graphpad Prism) were used for multiple group analyses. Data are presented as the mean±SEM; p<0.05 was considered significant.

Example 2. Pancreatic Phenotype of Fgf21-Knockout Mice

Figure 2:
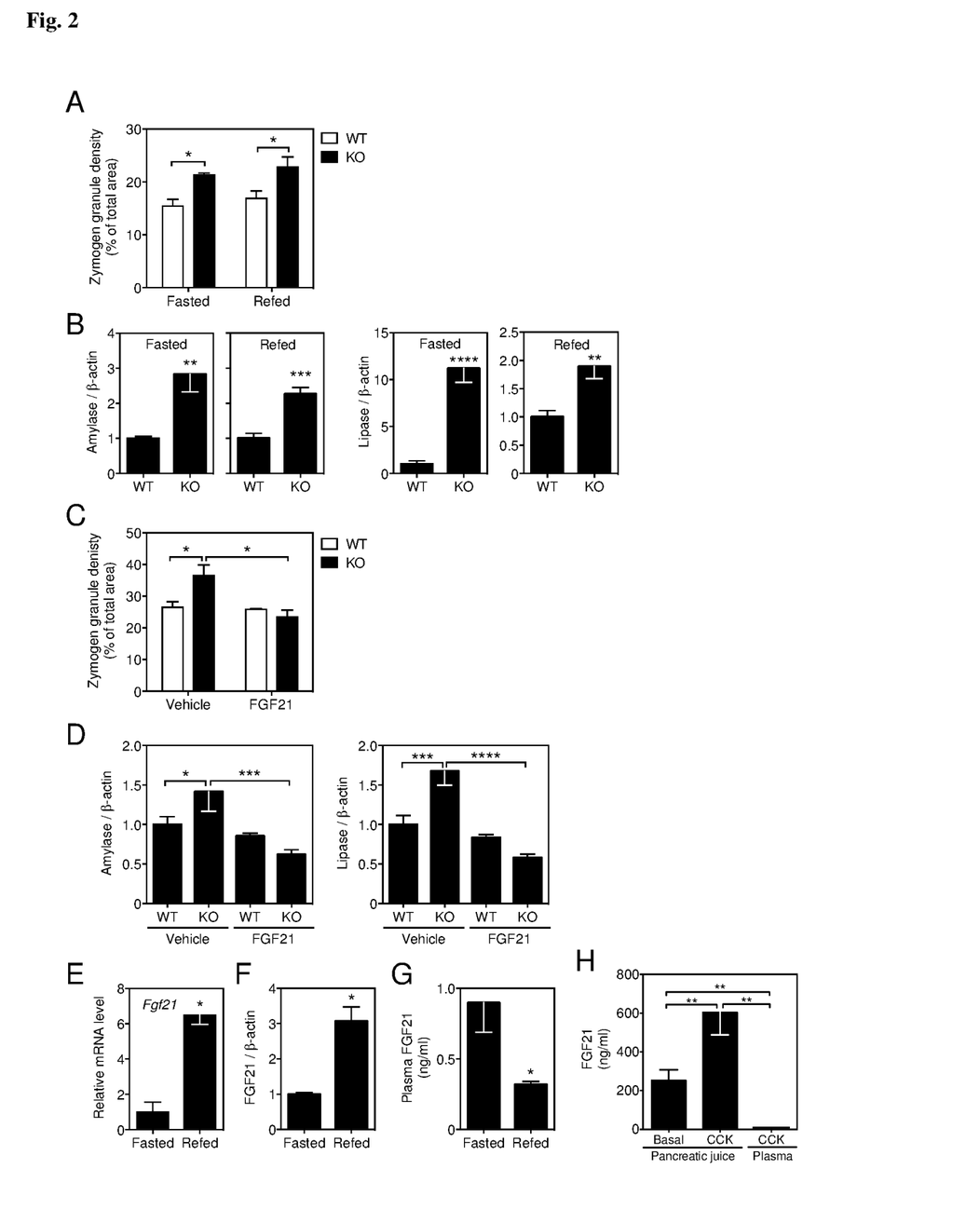

Fgf21-knockout (KO) mice were examined to determine whether they exhibit a pancreatic phenotype. Histological analysis of H&E-stained pancreatic sections revealed significantly greater eosinophilic staining in Fgf21-KO pancreas from both fasted and fed mice, indicative of increased zymogen granule density (FIG. 2A). In support of this observation, amylase and lipase levels were greater in Fgf21-KO pancreas during fasting and refeeding (FIG. 2B). Administration of exogenous FGF21 decreased the pancreatic eosinophilic area fraction in Fgf21-KO mice to wild type (WT) levels (FIG. 2C) Immunoblot analysis confirmed a corresponding reduction in pancreatic digestive enzyme levels in Fgf21-KO mice following FGF21 treatment (FIG.

2D). FGF21 mRNA and protein levels were induced in the pancreas during refeeding (FIGS. 2E and F). Notably, however, refeeding decreased FGF21 concentrations in plasma (FIG. 2G), demonstrating that FGF21 is not secreted from the exocrine pancreas into the blood. In contrast, observed a 200-fold higher level of FGF21 was observed in the pancreatic juice as compared to the plasma of ad-lib fed mice WT mice (FIG. 2H). Moreover, treatment with CCK, which is known to markedly increase pancreatic enzyme synthesis, resulted in a further 3-fold increase in the concentration of FGF21 in the pancreatic juice without any change in the blood (FIG. 2H). Thus, in response to physiologic and pharmacologic stress, FGF21 acts in an autocrine or paracrine manner to regulate pancreatic digestive enzyme levels.

Example 3. Effect of FGF21 on Pancreatic Protein Synthesis

Figure 3:
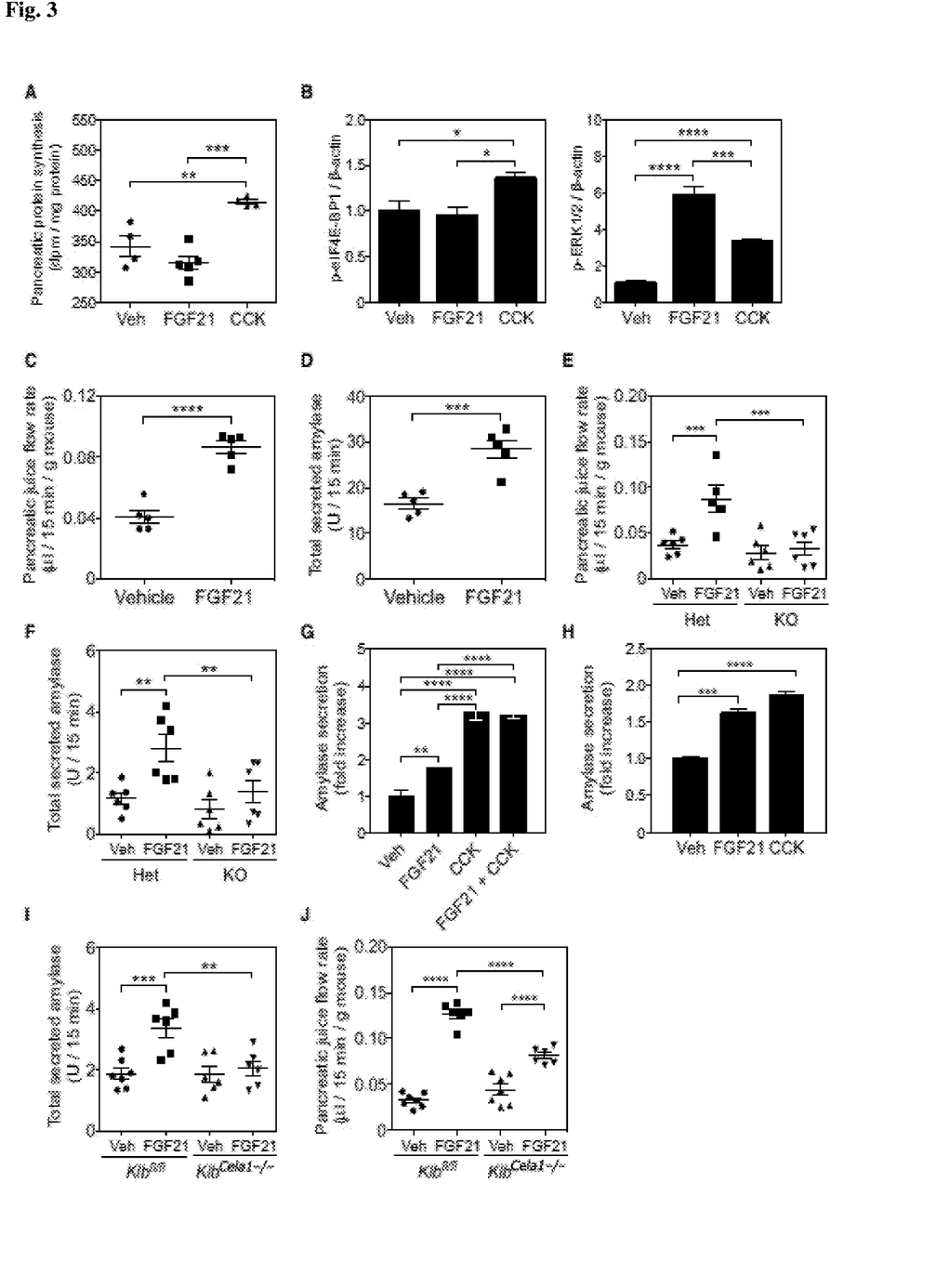
FIG. 3 shows that FGF21 Acts on Acinar Cells to Induce Pancreatic Digestive Enzyme Secretion without Affecting Protein Synthesis. (A and B) $^3$H-Phenylalanine incorporation into pancreatic protein (A) and western blot quantification of pancreatic phospho (p)-eIF4E-BP1 and p-ERK1/2 (B) in mice treated with vehicle, 1 mg/kg FGF21, or 5 mg/kg CCK for 2 hr (A) or 15 min (B). (C-F) Pancreatic juice flow rates and amylase levels in the pancreatic juice of WT mice (C and D) or heterozygous (Het) control or β-Klotho knockout (KO) mice (E and F) treated with vehicle or 1 mg/kg FGF21 for 2 consecutive days. (G and H) Amylase secretion from mouse primary acinar cells (G) and AR42J cells (H) treated with vehicle, 1 µg/mL FGF21, 10 pM (primary acinar cells), 100 pM (AR42J cells) CCK, or both 1 µg/mL FGF21 and 10 pM CCK (primary acinar cells) for 30 min (I and J) Amylase levels (I) and pancreatic juice flow rates (J) in the pancreatic juice of Klb$^{fl/fl}$ and Klb$^{Cela1-/-}$ mice treated with vehicle or 1 mg/kg FGF21 for 2 consecutive days. Results are expressed as means±SEM; n=4-6 mice/group for all experiments. Primary acinar cell experiments were performed in triplicate, and similar results were obtained in three independent experiments.*p<0.05; p<0.01; *p<0.001; ****p<0.0001.

FGF21 could reduce digestive enzyme concentrations in pancreatic acinar cells by either inhibiting protein synthesis or increasing their secretion. The effect of FGF21 on pancreatic protein synthesis in comparison to CCK was examined. As expected, CCK administration significantly increased $^3$H-phenylalanine incorporation into pancreatic protein (FIG. 3A). In contrast, FGF21 administration had no significant effect on pancreatic protein synthesis (FIG. 3A). Consistent with this protein synthesis profile, CCK increased phosphorylation of eukaryotic translation initiation factor 4E binding protein 1 (eIF4E-BP1), whereas FGF21 had no effect (FIG. 3B). Both FGF21 and CCK induced ERK1/2 phosphorylation in pancreas (FIG. 3B), demonstrating that they both signal in the pancreas. Therefore, FGF21 does not reduce digestive enzyme levels in the pancreas by suppressing protein synthesis. Moreover, unlike CCK, FGF21 does not stimulate pancreatic protein synthesis.

The FGF21 compound utilized in our studies was human recombinant FGF21 from Novo Nordisk. While this compound is the native form of the human FGF21 other FGF21 analogs and mimetics are available; all of them targeting the FGFR/β-Klotho receptor complex. Some of these FGF21 derivatives include, but are not limited to: LY2405319 (Lilly Research Laboratories), FGF21-mimetic monoclonal antibody mimAb1 (Amgen), PF-05231023 (Pfizer), FGF21-mimetic agonistic anti-FGFR1 (FGF receptor 1) antibodies R1MAbs (Genentech).

Example 4. Effect of FGF21 on Pancreatic Protein Secretion

Preparation of Murine Primary Acinar Cells

Primary acinar cells were prepared by modification of a published protocol (Williams, et al., *The American journal of physiology* 235, 517-524, 1978). Briefly, mice were sacrificed by decapitation followed by dissection and washing of the pancreas in 1× PBS. Pancreas digestion medium (0.75 mg/ml collagenase type XI-S [Sigma], 0.1 mg/ml soybean trypsin inhibitor [Sigma], 1% BSA in DMEM) was injected into the pancreatic parenchyma with a 30 g syringe. Pancreas was then incubated in digestion medium for 20-40 minutes with constant mixing using serological pipets of decreasing diameters. Cells were filtered through a 100 μm strainer and washed 3 times with incubation medium (0.1 mg/ml soybean trypsin inhibitor, 1% BSA in DMEM) via centrifugation at 50×g for 3 minutes per wash. Cells were plated and allowed to recover for 2 hours in incubation medium at 37° C.

Cell Secretion Assays

Primary acinar and AR42J cells were treated with vehicle, FGF21 (1 μg/ml for both primary acinar cells and AR42J) or CCK (10 pM for primary acinar cells and 100 pM for AR42J cells [Phoenix Pharmaceuticals]) for 30 minutes at 37° C. Amylase levels in both the cell medium and cells were analyzed using an Amylase Assay Kit (Abcam).

Calcium Imaging

AR42J cells were pre-loaded with 1 μM of the calcium indicator fluo4-AM (Life Technologies) for 30 minutes at 37° C. Where indicated, 1 μM PD173074 (Sigma), 10 μM L-364,718 (Tocris Bioscience), 10 μM U73122 (Tocris Bioscience) or 100 μM 2-APB (Tocris Bioscience) were added during fluo4-AM preloading and to the imaging medium (DMEM without phenol red). Cells were imaged on a BD Pathway 855 bioimager with a 10×objective. Vehicle, FGF21 (1 μg/ml) and CCK (100 pM) were delivered 10 seconds after baseline fluorescence acquisition by an automated fluid delivery mechanism and imaged for a total time of 2 minutes. Calcium release was calculated using Image J as ΔF/F0, where ΔF is the raw fluorescent signal (F) from cells minus their background fluorescence (calculated from a region where no cells and fluorescent signal was expected), and F0 was the average of the first 6 frames before the compound was added. Sample size (n) corresponds to the number of cell clusters measured with each cell cluster containing 5-20 cells.

To explore whether FGF21 also acts directly on pancreatic acinar cells in vivo, we generated an inducible acinar cell-specific β-Klotho (Klb) knockdown mouse model in which Cre recombinase expression was under the control of a modified estrogen receptor and the elastase promoter. Efficient knockdown of Klb expression following tamoxifen administration was confirmed in floxed Klb mice carrying the Cre allele (Klb$^{Cela1-/-}$). There was no change in plasma FGF21 concentrations in Klb$^{Cela1-/-}$ mice under fasted conditions. Similar to the Fgf21 KO mice, the Klb$^{Cela1-/-}$ mice had increased zymogen granule density and pancreatic digestive enzyme concentrations. To test whether FGF21 acts directly on pancreatic acinar cells to stimulate secretion, Klb$^{fl/fl}$ and Klb$^{Cela1-/-}$ mice were treated with either vehicle or FGF21 and pancreatic juice collected for 15 min. The effect of FGF21 on digestive enzyme secretion was absent in Klb$^{Cela1-/-}$ mice (FIG. 3I), and the effect on pancreatic juice flow rate was significantly reduced but not eliminated (FIG. 3J). Regarding this latter result, we did not detect β-Klotho expression in pancreatic ductal epithelial cells using knockin mice expressing a fusion of β-Klotho and TdTomato, indicating that FGF21 does not act directly on ductal cells. Moreover, FGF21 did not increase blood concentrations of secretin, an intestinal hormone that acts on pancreatic duct cells to induce pancreatic juice flow. Thus, the basis for the remaining effect of FGF21 on pancreatic juice flow rate requires further investigation. Nevertheless, the data demonstrate that FGF21 acts directly on pancreatic acinar cells to stimulate both juice flow and digestive enzyme secretion.

Example 5. FGF21 Signaling

Figure 4:
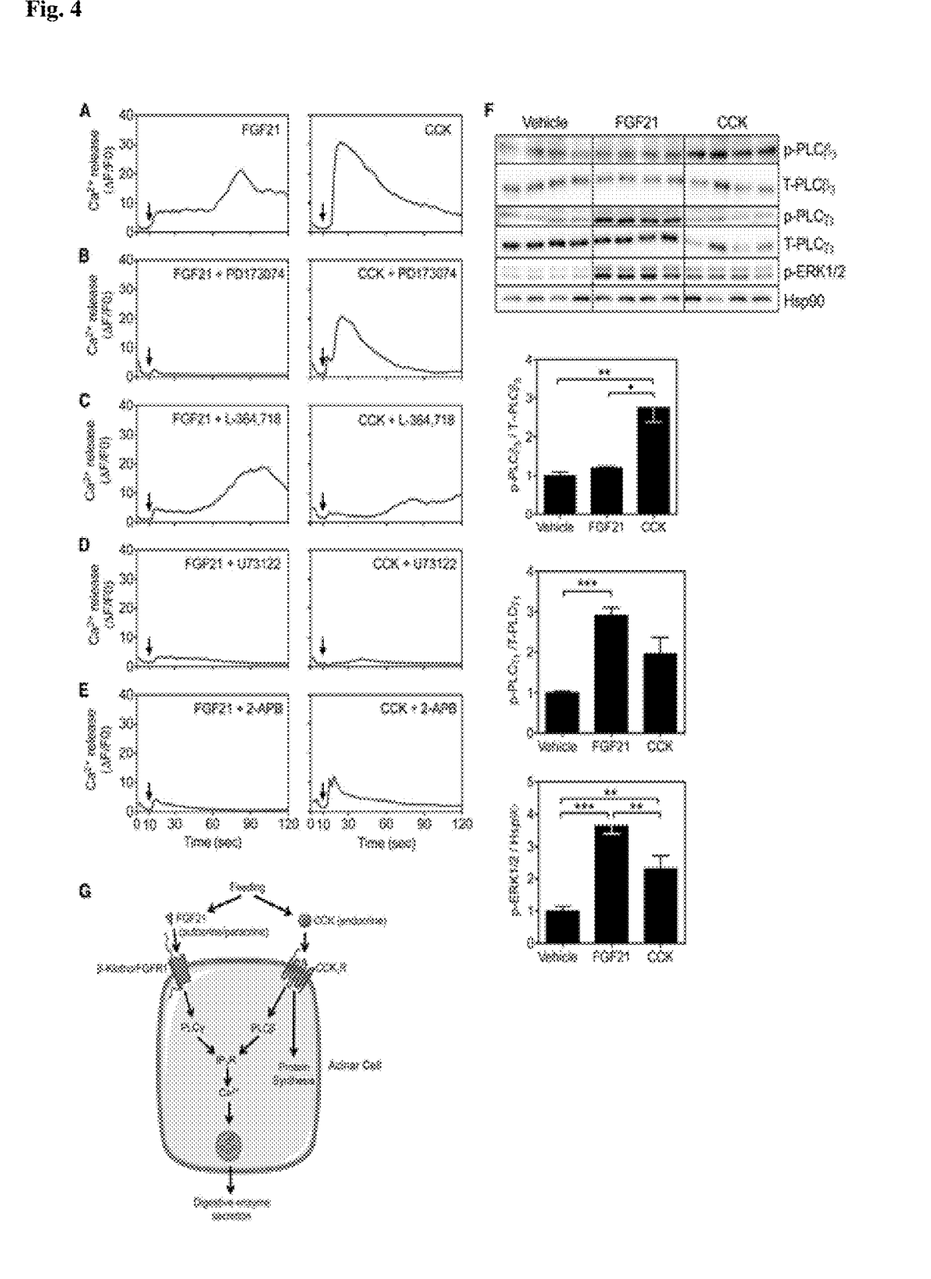
Figure 5:
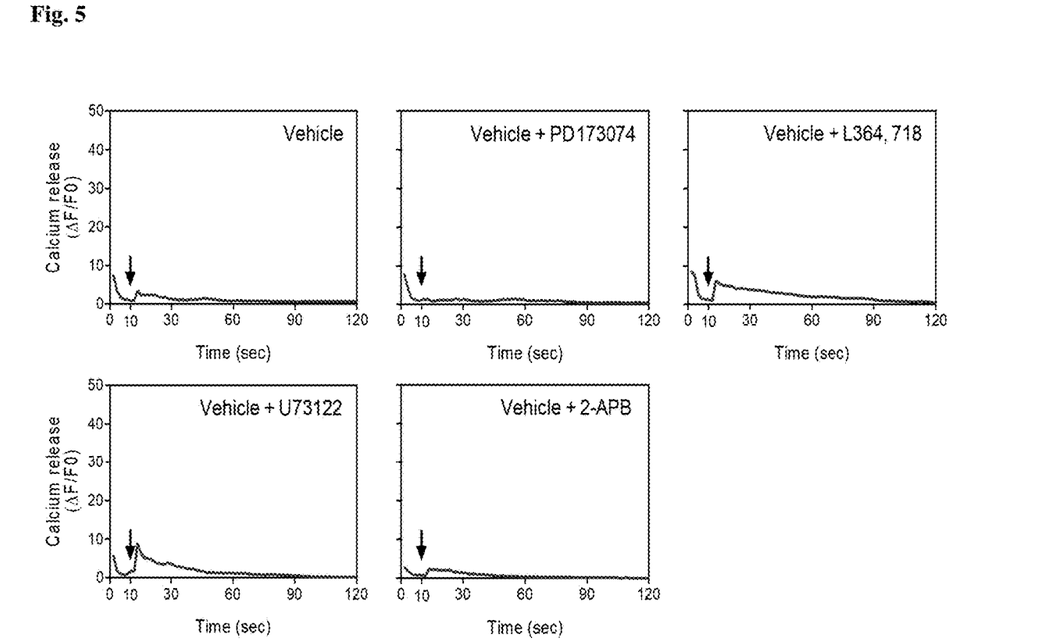

CCK stimulates secretion from the exocrine pancreas by activating a phospholipase C (PLC)-inositol triphosphate receptor (IP3R) signaling cascade that induces intracellular calcium release from the ER. The FGF21 co-receptor, FGFR1, which is expressed in the exocrine pancreas also activates PLC, suggesting that FGF21 might act through a similar mechanism. In support of this, treatment of AR42J cells with either FGF21 or CCK triggered intracellular calcium release (FIG. 4A). Interestingly, the calcium release profile was dynamically and temporally distinct upon treatment with FGF21 compared to CCK: whereas calcium levels peaked within 30 seconds after CCK treatment, the effect of FGF21 was more sustained, with calcium levels peaking 1-2 minutes after treatment (FIG. 4A). The calcium release elicited by FGF21 was blocked by the FGF receptor antagonist PD173074 but not the CCK-A receptor antagonist L-364,718; conversely, CCK-mediated calcium release was blocked by L-364,718 but not PD173074 (FIGS. 4B and C). Treatment of AR42J cells with either the PLC inhibitor U73122 or the IP3R inhibitor 2-APB blocked calcium release elicited by both FGF21 and CCK (FIGS. 4D and E). None of the inhibitors affected calcium release on their own (FIG. 5). Collectively, these data demonstrate that FGF21 and CCK act through different cell surface receptors to engage downstream PLC-IP3R pathways and elicit calcium release in pancreatic acinar cells.

Activation of the CCK-A receptor leads to the phosphorylation of the b isoform of PLC, calcium release, and subsequent secretion. In contrast, FGF receptors activate the γ isoform. To explore whether FGF21 and CCK have different activation profiles for the PLC isoforms, we treated WT mice with vehicle, FGF21, or CCK for 15 min. As expected, CCK induced the phosphorylation of PLCβ (FIG. 4F). In contrast, FGF21 induced the phosphorylation of PLCγ (FIG. 4F). Both FGF21 and CCK induced ERK1/2 phosphorylation demonstrating that signaling was active in the pancreas at 15 min following administration of either CCK or FGF21 (FIG. 4F). Collectively, these data show that FGF21 and CCK act through different cell-surface receptors and PLC isoforms to engage downstream $IP_3R$-mediated calcium release in pancreatic acinar cells.

Example 6. Role of FGF21 in Pharmacologic-Induced Pancreatitis

Figure 6:
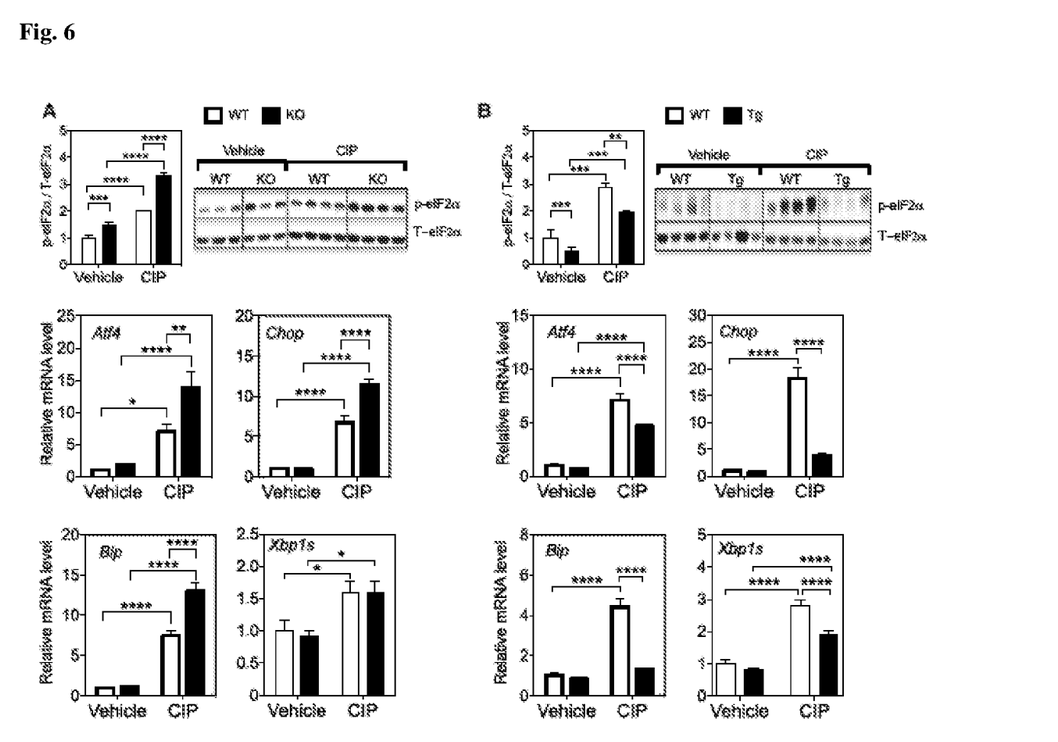
FIG. 6 shows that FGF21 attenuates ER stress during cerulein-induced pancreatitis. (A, B) Quantification of p-eIF2α protein and Atf4, Chop, Bip, and XBP1s mRNA analyzed by qPCR in wild-type (WT) and Fgf21-knockout (KO) mice (A) or WT and Fgf21-transgenic (Tg) mice (B) treated with cerulein to induce pancreatitis (CIP). Results are expressed as means±S.E.M. n=3-6 mice/group for all experiments. *, p<0.05; , p<0.01; *, p<0.001; ****, p<0.0001.

FGF21 protects mice against pancreatitis induced by the potent CCK analog cerulein. However, the mechanism underlying this beneficial effect is not known. It was investigated whether FGF21 protects against cerulein-induced pancreatitis (CIP) by stimulating pancreatic secretion, thereby attenuating ER stress and tissue damage. CIP was induced in WT and Fgf21-KO mice and markers of ER stress were measured, including phosphorylation of the subunit of eukaryotic translation initiation factor 2 (eIF2) and induction of activating transcription factor 4 (Atf4), CCAAT-enhancer-binding protein homologous protein (Chop) and immunoglobulin-heavy-chain-binding protein (Bip). CIP elicited a strong ER stress response in pancreas of both WT and Fgf21-KO mice (FIG. 6A). However, ER stress was exacerbated in the Fgf21-KO mice, as evidenced by significantly greater levels of phosphorylated eIF2 and Atf4, Chop and Bip mRNA (FIG. 6A). Conversely, chronic administration of FGF21, using a liver-specific transgene that elevates circulating FGF21 to supraphysiologic levels, suppressed these ER stress parameters in response to CIP (FIG. 6B). These data suggest that FGF21 mitigates pharmacologic-induced pancreatic ER stress, thereby restoring proteostasis in the acinar cells.

The present invention shows for the first time that FGF21 acts via an autocrine or paracrine signaling mechanism on pancreatic acinar cells to stimulate zymogen secretion and pancreatic juice flow. Like the prototypical pancreatic secretagogue, CCK, FGF21 induces secretion by activating PLC/IP3R signaling and calcium release. Importantly, however, FGF21 acts through a receptor complex distinct from that of CCK and does not concomitantly induce protein synthesis. As a consequence, unlike CCK, FGF21 alleviates ER stress that can occur in pancreas under either physiological conditions such as fasting/refeeding or pathological conditions such as pancreatitis.

Example 7. Endoscopic Retrograde Cholangiopancreatography

To evaluate if FGF21 confers a beneficial effect against ERCP-induced pancreatitis, a preclinical study was performed in an established rodent model of ERCP that develops pancreatitis 24 hours after ERCP. Female Swiss Webster mice were treated with either 4 subcutaneous injections of vehicle or 1 mg/kg FGF21 in the following way: 1 injection the day prior to ERCP, 2 injections the day of the ERCP procedure, and 1 injection the day following ERCP. Mice were subjected to the ERCP procedure, which consisted of a high-pressure infusion of a radiocontrast agent through the pancreatic duct. Histological grading of the pancreas of mice revealed that FGF21 decreased both the edema and inflammation after ERCP.

FGF21 or a derivative thereof according to the present invention is administered to a subject suffering from EPI subsequent to ERCP, resulting in increased secretion without increased protein synthesis, thus treating the underlying causes of EPI and acting to resolve ER stress.

FGF21 or FGF21 derivatives may be administered prophylactically (before ERCP), during the procedure, or following the procedure by oral, intravenous or intramuscular injections. Typical dosing may be between 0.1-300 mg depending on the pharmacokinetics of the individual FGF21 analogs. For example, dosing may be between 1-200 mg, 10-150 mg, or 50-100 mg, according to the FGF21 analog to be used.

Example 8. Pancreatitis

FGF21 or a derivative thereof according to the present invention is administered to a subject suffering from pancreatitis, resulting in increased secretion without increased protein synthesis, thus treating the underlying causes of the pancreatitis and acting to resolve ER stress.

FGF21 or FGF21 derivatives will be administered by oral, intravenous or intramuscular injections. Typical dosing may be between 0.1-300 mg depending on the pharmacokinetics of the individual FGF21 analogs. For example, dosing may be between 1-200 mg, 10-150 mg, or 50-100 mg, according to the FGF21 analog to be used.

Example 9. Exocrine Pancreatic Insufficiency

FGF21 or a derivative thereof according to the present invention is administered to a subject suffering from EPI, resulting in increased secretion without increased protein synthesis, thus treating the underlying causes of EPI and acting to resolve ER stress.

FGF21 or FGF21 derivatives will be administered by oral, intravenous or intramuscular injections. Typical dosing may be between 0.1-300 mg depending on the pharmacokinetics of the individual FGF21 analogs. For example, dosing may be between 1-200 mg, 10-150 mg, or 50-100 mg, according to the FGF21 analog to be used.

The invention claimed is:

1. A method of increasing exocrine pancreatic secretion in a subject in need thereof, comprising administering to said subject a therapeutically sufficient amount of fibroblast growth factor 21 (FGF21) or a derivative of FGF21.

2. The method of claim 1, wherein administering comprises local, regional, or systemic administration.

3. The method of claim 2, wherein administering comprises providing a single dose.

4. The method of claim 2, wherein administering comprises oral, intravenous or intramuscular administration.

5. The method of claim 1, wherein the FGF21 or FGF21 derivative is administered at a dosage of between 0.1 mg and 300 mg.

6. The method of claim 5, wherein the FGF21 or FGF21 derivative is administered at a dosage of between 1 mg and 200 mg.

7. The method of claim 1, wherein the derivative of FGF21 is a long-acting derivative of FGF21.

8. The method of claim 1, wherein administering comprises providing a pharmaceutical composition comprising FGF21 or a derivative of FGF21, dispersed in a pharmaceutically acceptable carrier, buffer or diluent.

9. The method of claim 1, further comprising providing to the subject a second therapy.

10. The method of claim 9, wherein the second therapy is provided prior to administering the FGF21 or derivative of FGF21.

11. The method of claim 9, wherein the second therapy is provided after administering the FGF21 or a derivative of FGF21.

12. The method of claim 9, wherein the second therapy is provided at the same time as the FGF21 or a derivative of FGF21.

13. The method of claim 1, wherein said subject is a human.

14. The method of claim 1, wherein the subject has pancreatitis.

15. The method of claim 14, wherein the pancreatitis is chronic.

* * * * *